United States Patent [19]
Tepper et al.

[11] Patent Number: 6,112,108
[45] Date of Patent: Aug. 29, 2000

[54] METHOD FOR DIAGNOSING MALIGNANCY IN PELVIC TUMORS

[75] Inventors: Ron Tepper, Herzlia; Solange Akselrod, Ramat Ilan, both of Israel

[73] Assignee: Ramot University for Applied Research & Industrial Development Ltd., Tel Aviv, Israel

[21] Appl. No.: 08/928,472

[22] Filed: Sep. 12, 1997

[51] Int. Cl.[7] .................................................. A61B 5/05
[52] U.S. Cl. ........................ 600/407; 600/454; 600/411
[58] Field of Search .................................. 600/407, 410, 600/419, 454, 457, 504, 310, 455, 425, 427, 431, 436, 411, 473, 475, 476, 477

[56] References Cited

U.S. PATENT DOCUMENTS

| | | | |
|---|---|---|---|
| 3,771,355 | 11/1973 | Sachs | 73/67.5 |
| 4,059,010 | 11/1977 | Sachs | 73/596 |
| 4,782,840 | 11/1988 | Martin et al. | 600/436 |
| 5,014,715 | 5/1991 | Chapolini | 600/485 |
| 5,260,050 | 11/1993 | Ranney | 424/9 |
| 5,352,979 | 10/1994 | Conturo | 324/307 |
| 5,402,785 | 4/1995 | Leigh et al. | 600/410 |
| 5,595,721 | 1/1997 | Kaminski et al. | 424/1.49 |
| 5,789,921 | 8/1998 | Albert et al. | 324/300 |
| 5,800,350 | 9/1998 | Coppleson et al. | 600/372 |

OTHER PUBLICATIONS

Kim et al., Quantative determination of tumor blood flow and perfusion via deuterium nuclear magnetic resonance spectroscopy in mice, Cancer Res., Jun. 15 1988, 48 (12), p3449–53.

Thompson et al, "Doppler Ultrasound Waveform Indices: A/B Ratio, Pulsatility Index and Pourcelot Ratio", *Brit. J. Obstetrics and Gynacology*, 95: 581–588, 1988.

Folkman et al, "Induction of Angeogenesis During the Transition from Hyperplasia to Neoplasia", *Nature*, 339: 58–61, 1989.

Kawai et al, "Transvaginal Doppler Ultrasound with Color Flow Imaging in the Diagnosis of Ovarian Cancer", *Obstetrics and Gynacology*, 79(2): 163–166, 1992.

Kurjak et al, "Transvaginal Ultrasound, Color Flow, and Doppl;er Waveform of the Postmenopausal Adnexal Mass", *Obstetrics and Gynacology*, 80(6): 917–920, 1992.

Tepper et al, "Transvaginal Color Flow Imaging in the Diagnosis of Ovarian Tumors", *J. Ultrasound Med*, 14:731–734, 1995.

Weiner et al, "Differentiating Malignant from Benign Ovarian Tumors with Transvaginal Color Flow Imaging", *Obstetrics and Gynacology*, 79(2): 159–162, 1992.

Shimamoto et al, "Intratumoral Blood Flow: Evaluation with Color Doppler Echography", *Cardiovasular Radiology*, 165: 683–685, 1987.

Tepper et al, "Transvaginal Color Doppler Ultrasound in the Assessement of Invasive Cervical Carinoma", *Gynecologic Oncology*, 60: 26–29, 1996.

Bourne et al, "Transvaginal Color Flow Imaging: A Possible New Screening Technique for Ovarian Cancer", *Br. Med. J.*, 299: 1367–1370, 1989.

Bromley et al, "Comparison Between Sonographic Morphology and Doppl;er Waveform for the Diagnosis of Ovafrian Malignancy", *Obstetrics and Gynacology*, 83: 434–437, 1994.

(List continued on next page.)

*Primary Examiner*—Brian L. Casler
*Attorney, Agent, or Firm*—Mark M. Friedman

[57] ABSTRACT

A method for diagnosing malignancy in a tumor. A waveform representative of pulsatile blood flow in the tumor is measured, and the post-systolic portion of the wave form is fit with a mathematical function such as an exponential decay curve. A decay constant greater than about 48 pixels is diagnostic of malignancy.

16 Claims, 4 Drawing Sheets

OTHER PUBLICATIONS

Valentin et al, "Limited Contribution of Doppler Velocimetry to the Differential Diagnosis of Wxtrauterine Pelvic Tumors", *Obstetrics and Gynacology*, 83: 425–433, 1994.

Hamper et al, "Transvaginal Color Doppler Sonography of Adnexal Masses: Differences in Blood Flow Impedance in Benign and Malignant Lesions", *AJR*, 160: 1225–1228, 1993.

Walsh et al, "An Index of Peripheral Vascular Resistance", *Healthgate Document*, healthgate.com (abstract) 1985.

Yin et al, "Estimating Arterial Resistance and Compliance During Transient Conditions in Humans", *Healthgate Document*, healthgate.com (abstract) 1989.

Thompson et al, "Doppler Ultrasound Waveforms in the Fetal Umbilical Artery: Quantitative Analysis Technique", *Ultrasound in Med. & Biol.*, 11(5): 707–718, 1985.

Salem, S., "What is Doppler's Role in Adnexal Masses?", *Diagnostic Imaging Europe*, F19–F26, 1996.

Figure 4 The Decay Curve

METHOD FOR DIAGNOSING MALIGNANCY IN PELVIC TUMORS

FIELD AND BACKGROUND OF THE INVENTION

The present invention relates to the process of diagnosing malignant tumors and, in particular, it concerns a method and system for screening patients with gynecologic tumors so as to determine whether such tumors are likely to be benign or malignant.

It is known that ovarian malignancies represent the primary cause of mortality due to gynecological cancer (D. W. Cramer, "Epidemiologic and statistical aspects of gynecologic oncology," in: R. C. Knapp and R. S. Berkowitz, eds. *Gynecologic Oncology.* New York: McMillian, 1986). As tumors of this nature may remain quiescent for long periods of time, patients with ovarian malignancies are often diagnosed late in the course of their disease (S. Salem, "What is Doppler's role in adnexal masses?" *Diagnostic Imaging Europe,* December 1996: F19–F26). The initial diagnosis of an ovarian or other pelvic mass (by which is meant any tumor manifesting in the area of the female reproductive system) is usually rapidly confirmed by a gynecological ultrasound examination. The question then arises as to whether or not the tumor is malignant, the implication of which being that immediate and extensive surgery and chemotherapy may be necessary. Immediate surgical biopsy of all pelvic tumors at the time of initial diagnosis so as to rule out malignancy would be unnecessarily invasive in most cases, however as the majority of such tumors are, in fact, benign. Effort has therefore been directed not only at the early diagnosis of pelvic cancer, but also at the development of non-invasive screening techniques to identify which pelvic tumors are possibly malignant and warrant immediate surgical biopsy. As diagnostic gynecologic ultrasound is universally indicated for all patients with suspected pelvic malignancy, it is the ideal non-invasive diagnostic modality for such screening, which could then be performed at the time of initial diagnosis. Unfortunately, although ultrasound is highly accurate in detecting the presence of pelvic masses, the ultrasound appearance of such masses is often non-specific with regard to the likelihood of malignancy. Ancillary ultrasound indicators of malignancy in pelvic tumors have thus been investigated, in an attempt to improve the specificity of ultrasound as a screening technique.

Indirect evidence of malignancy may be inferred from the nature of blood-flow through malignant tissue. Because malignant tissue grows in a rapid and haphazard fashion, angiogenesis within such tumors tends to be abnormal (J. Folkman, "Tumor Angiogenesis," in: *Advances in Cancer Research,* 1985, vol. 43:175–203; J. Folkman, K. Watson, D. Ingber, and D. Hanahan, "Induction of angiogenesis during the transition from hyperplasia to neoplasia," *Nature.* 1989;339:58–61), resulting in blood vessels and capillaries which are more dilated than usual. The vasculature of malignant tissue thus presents less impedance (by which is meant vascular resistance) to blood-flow than does the normal capillary bed found in a benign tumor. Lower vascular impedance may result in a higher diastolic flow velocity (R. S. Thompson, B. J. Trudinger and C. M. Cook. "Doppler ultrasound waveform indices: A/B ratio, pulsatility index and Pourcelot ratio," *Br J Obstet Gynaecol.* 1988;95:581–8. M. Kawai, T. Kano, F. Kikkawi, O. Maeda, H. Oguchi, and Y. Tomada, "Transvaginal Doppler ultrasound with color flow imaging in the diagnosis of ovarian cancer," *Obstet Gynecol.* 1992;79:163–7. A. Kurjak, H. Schulman, A. Sosic, I. Zalud, and H. Shalan, "Transvaginal ultrasound, color flow and Doppler waveform of the postmenopausal adnexal mass," *Obstet Gynecol.* 1992;80:917–21. R. Tepper, L. Lerner-Geva, M. Altaras, S. Goldberger, G. Ben-Baruch, S. Markov, I. Cohen, and Y. Beyth, "Transvaginal color flow imaging in the diagnosis of ovarian tumors," *J Ultrasound Med.*1995; 14:731–734. Z. Weiner, I. Thaler, D. Beck, S. Rottem, M. Deutsch, and J. M. Brandes, "Differentiating malignant from benign ovarian tumors with transvaginal color flow imaging," *Obstet Gynecol.* 1992;79:159–62.). Doppler techniques have therefore been used to evaluate the nature of diastolic flow within pelvic tumors as a means of inferring the vascular impedance, and thus the likelihood of malignancy, of such tumors. To date, flow impedance has been inferred from Doppler flow tracings by calculating either the pulsatility index (PI) or the resistive index (RI). The PI is derived from the following formula: peak systolic velocity minus end diastolic velocity divided by the mean velocity. The RI is peak systolic velocity minus end diastolic velocity divided by the peak systolic velocity.

The utility of both the PI and the RI as indicators of ovarian malignancy has been extensively investigated (R. K. Goswami, G. Williams, and P. C. Stepto, "Decreased uterine perfusion: a cause of infertility," *Hum Reprod.* 1988;3:955–9. K. Shimamoto, S. Sukuma, T. Ishigaki, and N. Makino, "Intratumoral blood flow: evaluation with color Doppler echography," *Radiology.*1987;165:683–5. R. Tepper, M. Altaras, S. Goldberger, Y. Zalel, M. Cordoba, and Y. Beyth, "Color Doppler ultrasonographic findings in low and high grade endometrial stromal sarcomas," *J Ultrasound Med.* 1994; 13:817–819. R. Tepper, L. Lerner-Geva, M. Altaras, S. Goldberger, G. Ben-Baruch, S. Markov, I. Cohen, and Y. Beyth, "Transvaginal color flow imaging in the diagnosis of ovarian tumors," *J Ultrasound Med.* 1995; 14:731–734. R. Tepper, Y. Zalel, M. Altaras, G. Ben-Baruch, and Y. Beyth, "Transvaginal color Doppler ultrasound in the assessment of invasive cervical carcinoma," *Gynecologic Oncology.* 1996;60:26–29.). Although initial reports were encouraging, more extensive reviews have shown that both the PI and the RI are, in fact, unreliable predictors of the presence of malignancy at biopsy (T. Bourne, S. Campbell, C. Steer, M. I. Whitehead, and W. P. Collins, "Transvaginal color flow imaging: a possible new screening technique for ovarian cancer," *Br Med J.* 1989;299:1367–70. B. Bromley, H. Goodman, and B. Banacerraf, "Comparison between sonographic morphology and Doppler waveform for the diagnosis of ovarian malignancy," *Obstet Gynecol.* 1994;83:434–7. R. Tepper, L. Lerner-Geva, M. Altaras, S. Goldberger, G. Ben-Baruch, S. Markov, I. Cohen, and Y. Beyth. "Transvaginal color flow imaging in the diagnosis of ovarian tumors," *J Ultrasound Med.* 1995; 14:731–734. L. Valentin, P. Sladkevicius, and K. Marsal, "Limited contribution of Doppler velocimetry to differential diagnosis of extrauterine pelvic tumors," *Obstet Gynecol.*1994;83:425–33. U. M. Hamper, S. Sheth, F. M. Abbas, N. B. Rosenshein, D. Aronson, and R. J. Kurman, "Transvaginal color Doppler sonography of adnexal masses: differences in blood flow impedance in benign and malignant lesions," *AJR* 1993;160:1225–8. A. Tekay and P. Joupilla, "Validity of pulsatility and resistance indices in classification of adnexal tumors with transvaginal color Doppler ultrasound," *Ultrasound Obstet Gynecol.* 1992;2:338–44.). As there are no other effective screening tests available, many patients with suspected ovarian or other pelvic malignancy still undergo unnecessary surgical biopsy.

There is therefore a need for a new, reliable, non-invasive method for assessing the likelihood of malignancy of pelvic tumors.

SUMMARY OF THE INVENTION

The present invention is a method for assessing the likelihood that a pelvic tumor is malignant, and a system for implementing such a method. The method includes the calculation of an indicator of vascular impedance which is an innovation in the field of tumor diagnosis, and is independent of the RI and PI: the time-decay constant of a post-systolic tumor blood-flow waveform. The system consists of the combination of a mechanism for obtaining a blood-flow waveform associated with a tumor with a mechanism for delineating the waveform and calculating the time-decay constant therefrom. This latter mechanism will hereinafter be referred to as a waveform delineator.

According to the teachings of the present invention, there is provided a method for diagnosing a tumor, including the steps of measuring a pulsatile blood-flow waveform associated with the tumor, fitting a post-systolic portion of the blood-flow waveform to a parameterized monotonic mathematical function, and inferring a characteristic of the tumor from a parameter of the monotonic mathematical function. There is further provided a method for diagnosing a pelvic tumor, including the steps of measuring a pulsatile blood-flow waveform associated with the pelvic tumor, fitting a post-systolic portion of the blood-flow waveform to a parameterized monotonic mathematical function, and inferring a characteristic of the pelvic tumor from a parameter of the monotonic mathematical function. There is also provided a system for diagnosing a tumor, including a mechanism for obtaining a blood-flow waveform for blood-flow associated with the tumor, a mechanism for fitting a post-systolic portion of the blood-flow waveform to a parameterized monotonic mathematical function, and a mechanism for determining a parameter of the parameterized monotonic mathematical function. There is further provided a system for diagnosing a pelvic tumor, comprising a mechanism for generating a blood-flow waveform for blood-flow associated with the pelvic tumor, a mechanism for fitting a post-systolic portion of the blood-flow waveform to a parameterized monotonic mathematical function, and a mechanism for determining a parameter of the parameterized monotonic mathematical function.

According to the teachings of the present invention there is therefore provided a method for diagnosing a tumor, e.g. a pelvic tumor, entailing measuring a pulsatile blood-flow waveform associated with the tumor, fitting a post-systolic portion of the blood-flow waveform to a parameterized monotonic mathematical function, and inferring a characteristic of the tumor from a parameter of the monotonic mathematical function. The method provides for deriving the blood-flow waveform from measurements of blood velocity, blood pressure, blood flow rate or other hemodynamic variables, by using Doppler techniques, ultrasound techniques, Magnetic Resonance Imaging techniques electromagnetic flow measurement techniques or intravascular catheterization techniques. Preferably, the parameterized monotonic mathematical function is an exponential decay curve, the parameter of the exponential decay curve is a decay constant, and the inferred characteristic of the tumor is vascular impedance or malignancy. There is further provided a system for diagnosing a tumor, including a pelvic tumor, including a mechanism for obtaining a blood-flow waveform for blood-flow associated with the tumor, a mechanism for fitting a post-systolic portion of the blood-flow waveform to a parameterized monotonic mathematical function, and a mechanism for determining a parameter of the parameterized monotonic mathematical function. Preferably, the mechanism for generating the blood-flow waveform includes a Doppler device, an ultrasound device, a Magnetic Resonance Imaging scanner, an electromagnetic flow measurement device or an intravascular catheterization device. The mechanism for fitting the post-systolic portion of the blood-flow waveform to the parameterized monotonic mathematical function includes a border detection algorithm.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a method and system for analyzing the blood-flow waveform of blood-flow associated with a tumor (by which is meant either blood-flow within a tumor, or blood-flow external to but related to a tumor—such as blood flowing towards a tumor), in a manner which results in the generation of a numerical parameter which predicts the likelihood that the vascular impedance of the tumor is low, thus implying the presence of malignant tissue within the tumor. In the preferred embodiment, the blood-flow waveform is derived by Doppler spectral interrogation of the blood velocity within a vessel, however in an alternative embodiment, the blood-flow waveform may be acquired by using other mechanisms for depicting intravascular hemodynamics, such as Magnetic Resonance Imaging (MRI) flow mapping. Such methods of MRI flow calculation are well described in the art. The vessels sampled are located either within or on the periphery of the tumor, or external to the tumor. In the preferred embodiment, the numerical parameter generated is the time decay constant of the post-systolic blood-flow decay curve. As broadly embodied herein, the method entails four processes:

1. Acquisition of a blood-flow waveform associated with the tumor by means of a mechanism for depicting intravascular hemodynamics
2. Transfer of the blood-flow waveform data to the waveform delineator
3. Delineation of the post-systolic portion of the waveform
4. Calculation of the time-decay constant of the post-systolic portion of the waveform.

The principles and operation of the method and system for diagnosing malignancy of a tumor, according to the present invention, may be better understood with reference to the drawings and the accompanying description.

Figure 1:
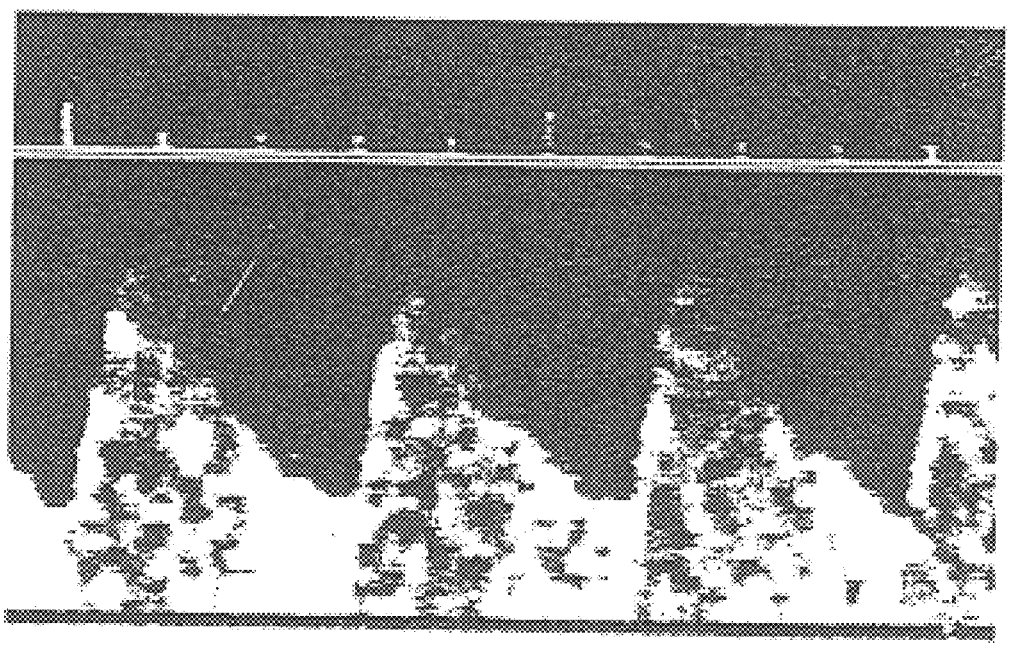
FIG. 1 is an example of Doppler spectral waveforms acquired from an ovarian tumor.

Referring now to the drawings, FIG. 1 demonstrates a spectral Doppler waveform depicting blood-flow through a vessel within a pelvic tumor.

Once acquisition of the Doppler waveforms has been accomplished, the flow-waveform data is transferred to the waveform delineator. The waveform delineator includes a computer micro-processor, a border detection algorithm, and a graphics card. A suitable computer for the waveform delineator is an at least 66 MHz IBM compatible PC with 8 megabytes of RAM. In the preferred embodiment, the waveform delineator is housed within the Doppler machine, and the Doppler waveform data is read directly into the waveform delineator from the computer processor of the Doppler machine. In an alternative embodiment, the waveform delineator is housed externally to the Doppler machine. In such a circumstance, the Doppler flow waveform data is stored on videotape, and transfer of the waveform data to the delineator entails utilizing an image grabbing algorithm as detailed as follows: The flow waveform patterns are selected from the video recordings, while freezing the image on a video player, and sampled into the waveform delineator using, for example, a DT2851 frame-grabber (Data Translation, Marlborough, Mass.) and an image processing board, achieving a resolution of 512×512 pixels and 256 gray levels. In an additional alternative embodiment, the waveform delineator is housed within the computer of an MRI scanner and signal processor. In such a circumstance, the waveform data derived from MRI measurements are read directly into the waveform delineator from the computer processor which performed the MRI flow calculation. In a further embodiment, the waveform delineator is housed externally to the MRI scanner computer. In this circumstance the flow waveform data acquired by MRI flow measurement is stored on a portable electronic data storage system such as an optical disk, video tape or floppy diskette, and then sampled into the waveform delineator from the storage system.

Figure 2:
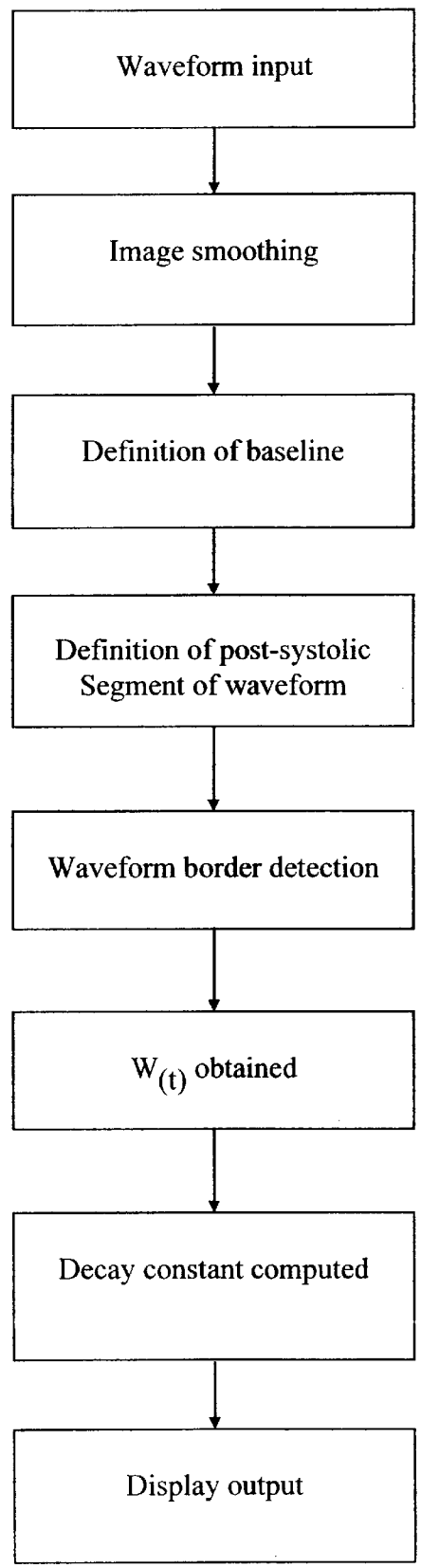
FIG. 2 is a flow chart of the functioning of a waveform delineator.

FIG. 2 is a flow chart depicting the functioning of the waveform delineator. In the preferred embodiment, the technique for waveform delineation is based on brightness differentiation of the pixels comprising a Doppler flow tracing. First, the image is smoothed by a square median filter, in order to remove signal "noise" and facilitate unambiguous detection of the region of the waveform border. A square median filter determines the median gray-scale value of each pixel by allocating to it the median value of the 8 surrounding pixels. This non-linear filter is more suitable than a linear low pass filter because it removes noise but still preserves the sharp edge of the Doppler signal. This edge is the flow waveform that will be delineated.

Once the image has been smoothed, automatic flow waveform detection is achieved by simple mathematical manipulation of the pixel gray levels. First, the user manually identifies the baseline of the Doppler flow tracing corresponding to zero velocity flow, for scaling purposes. Then the user selects a "region of interest" (ROI) in the region for which border detection is to be made, namely, the post-systolic portion of the waveform. On the Doppler flow tracing, the x coordinates represent time during the cardiac cycle, with the y coordinates representing the measured velocity of flow for each instant in time. As such, the tracing can be represented by a series of white "columns" on a black background, such that each column represents one x axis time interval. The height of each column is proportional to the measured flow velocity at that instant in time. The border detection algorithm functions by sequentially scanning column after column vertically from the baseline, determining the gray-scale value for each pixel until a minimum number of sequential black pixels have been detected. In the preferred embodiment, this minimum number is 15. The corresponding y-coordinate is taken to represent the transition area of the waveform. After subtracting the y-coordinate of the baseline level from the y-coordinate of the transition area for each column scanned, the wave form W(t) of the flow signal as a function of time is obtained. These values are then saved as an ASCII file, to be used as the input for the computation of the exponential decay.

Figure 3:
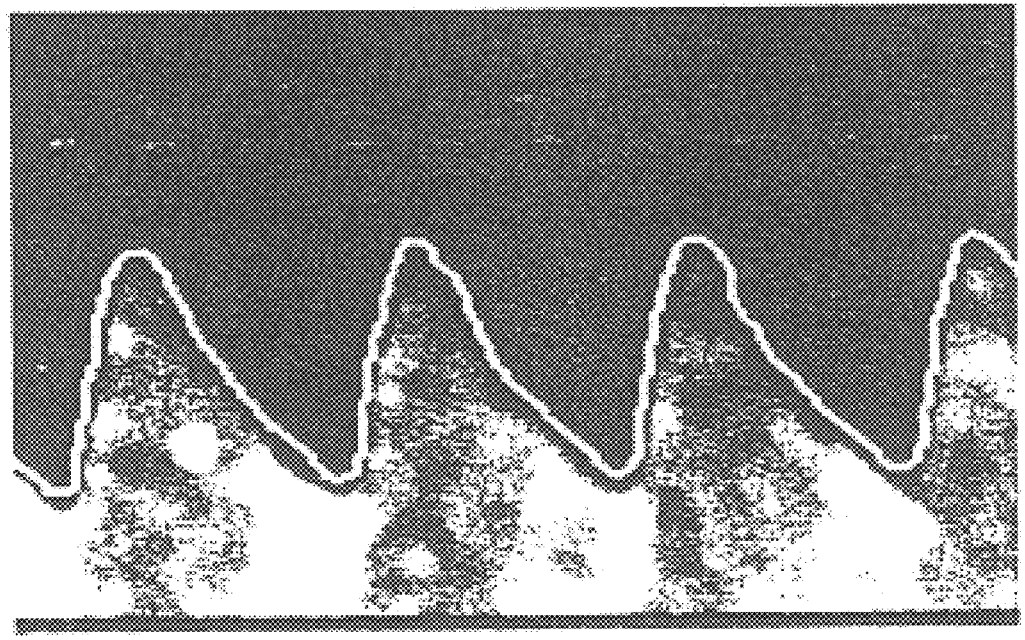
FIG. 3 shows the result of automatic processing of the Doppler waveforms shown in FIG. 1, after smoothing and edge detection have been performed.

FIG. 3 shows the result of automatic processing of the Doppler waveforms shown in FIG. 1, after smoothing and edge detection have been performed. The white curve is the waveform W(t).

In an alternative embodiment, the waveform W(t) as a function of time for MRI derived flow waveforms is computed by the waveform delineator from digital MRI waveform data, which is input to the waveform delineator from the computer of an MRI machine. In this instance, as the input data is already digital and describes the waveform W(t) as a function of time, a border detection algorithm is unnecessary.

Figure 4A:
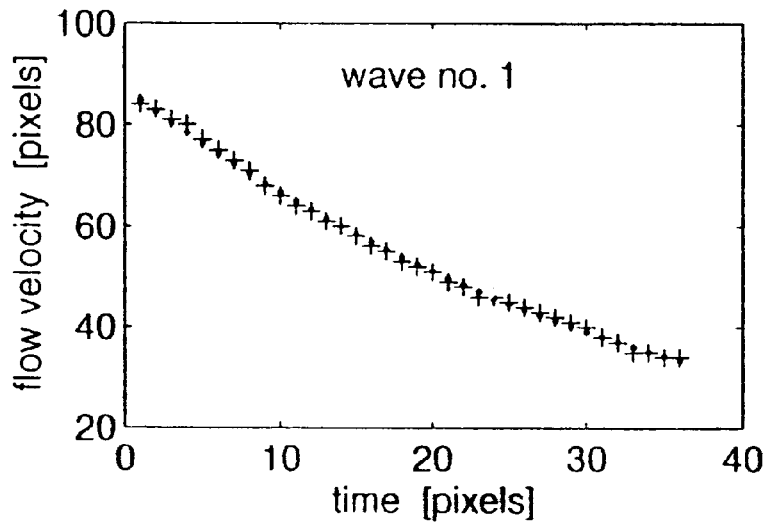
FIG. 4 shows the resultant exponential fit for the three wave-forms shown in FIG. 3.
Figure 4B:
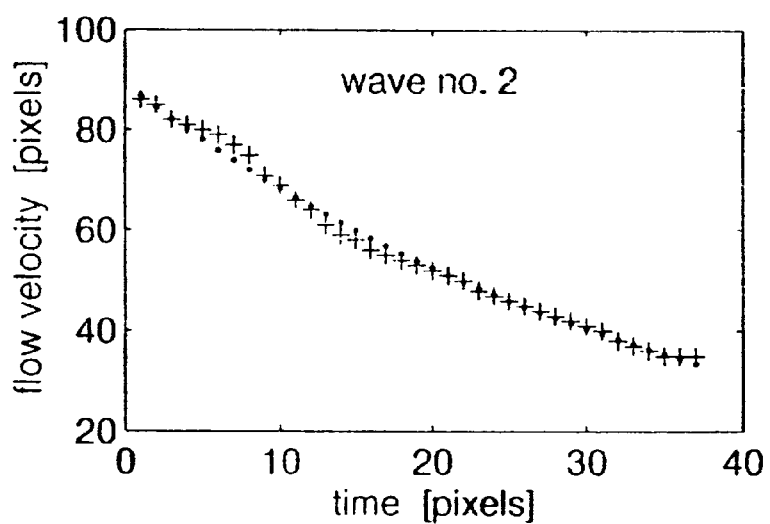
Figure 4C:
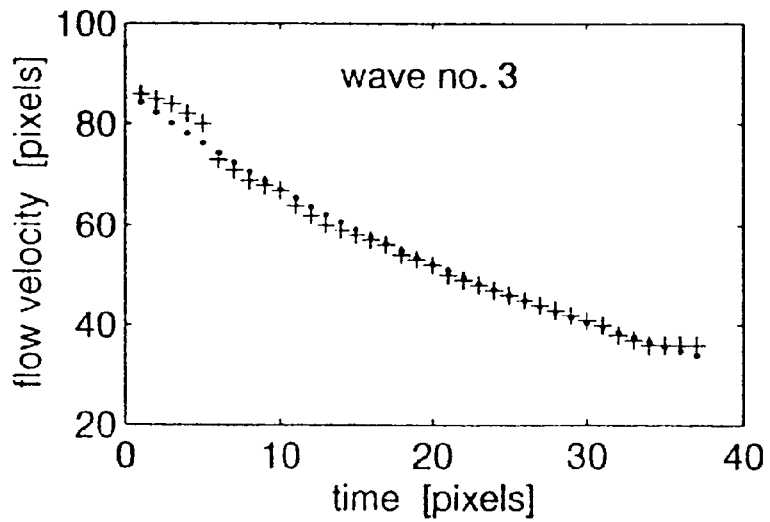

After determination of the W(t) curve, which digitally describes the flow wave-form, the waveform decay constant is computed. This constant is a mathematical parameter reflecting the rate of post-systolic decay of the flow wave. In the preferred embodiment the entire diastolic decay curve is used, from peak systole to end-diastole. In alternative embodiments, various different wave segments can be identified for determination of decay constants. A geometric algorithm in the computer of the waveform delineator calculates the decay constant by approximating the obtained waveform to an exponential curve using the "least mean square method", according to the following expression:

$$W(t) = Ke^{-t/\tau} + C$$

where:
- $\tau$—the post-systolic waveform decay constant
- C—the constant velocity towards which the waveform tends at infinity
- t—the time from peak systole
- K—a mathematical constant describing the initial flow level FIG. 4 shows the resultant exponential fit for the three wave-forms shown in FIG. 3. For each waveform, the "+" marks represent the detected flow waveform [the curve W(t)], while the "." marks provide the exponential curve formed using the obtained value of $\tau$ for the wave [the curve W(t)]. FIGS. 4(a), (b), and (c) correspond to the leftmost, middle, and rightmost wave-forms in FIGS. 1 and 3, respectively. In the preferred embodiment, C is taken to be zero. In alternative embodiments C is taken to be the end diastolic velocity or any value less than that. Rearrangement of the above equation then yields the post-systolic decay constant for the waveform. The resultant numerical value is displayed on a monitor of the waveform delineator.

Table 1 shows the results of preliminary experimentation with the post-systolic decay constant in patients with pelvic tumors. The decay constant was measured from the Doppler tracings of forty six patients with ovarian masses, who all subsequently underwent biopsy and histological diagnosis of the tumor. Group A consisted of patients proven by histology to have had primary ovarian malignancy, group B consisted of patients proven by histology to have had benign pelvic tumors, group C consisted of patients proven by histology to have had tumors exhibiting "low malignant potential" (LMP), group D consisted of patients proven by histology to have had metastatic tumors, and group E consisted of patients proven by histology to have had functional, non-tumorous, findings. As is shown in the table, the decay constants for groups A and B were markedly different, with this difference reaching statistical significance at a p value of <0.05. For the 21 post-menopausal patients in the cohort, a post-systolic decay constant value greater than 48 pixels had a positive predictive value of 80.7%, a negative predictive value of 47.4%, a sensitivity of 80%, and a specificity of 100% as an indicator of the presence or absence of malignancy. With the scaling used when analyzing these Doppler tracings, one pixel was equal to 11.4 milliseconds, indicating a malignancy threshold for the decay constant of about 0.5 seconds.

TABLE 1

Decay Constant (in pixels) in patients with pelvic tumors

| | Group A Malignant (n = 13) | Group B Benign (n = 14) | Group C LMP (n = 7) | Group D Metastastic (n = 4) | Group E Functional (n = 8) |
|---|---|---|---|---|---|
| mean | 89.7* | 41.8* | 54.4 | 56 | 67.2 |
| 95% CI | 60–119.3 | 25.7–57.9 | 34.5–73.4 | — | 43.7–90.7 |

CI—confidence interval
n—number of patients in each group
*significant difference (P < 0.05) between benign (Group B) and malignant tumors (Group A)

In the preferred embodiment, a decay constant greater than about 48 pixels indicates a high likelihood of malignancy.

In summary, then, the current invention provides a new method for non-invasively evaluating the likelihood of malignancy of a pelvic tumor. Although also based on an analysis of blood-flow patterns within a tumor, and thus, by inference, the vascular impedance of the tumor, the index used in the current invention (the decay constant) is independent of previously utilized indices of diastolic flow (the PI and RI). The decay constant is a more accurate index of vascular impedance than the PI and RI as both of the latter are dependent on 2 single point digitized measurements of velocity (at peak systole and end diastole), thus making them highly susceptible to random errors in digitization. The decay constant, in contrast, is derived entirely from multiple measurements along the full length of the blood-flow decay curve, thus minimizing the impact of random errors in waveform delineation. The present method for tumor screening can be easily and rapidly performed in a largely automated manner once the appropriate software has been incorporated into a standard gynecological ultrasound machine. This makes it an ideal method for bedside screening of newly diagnosed patients with pelvic tumors. Although the above description has related to the diagnosis of pelvic malignancies, it will be appreciated that the principles embodied therein are equally applicable to other solid tumors for which the malignant potential is unknown, regardless of their location in the body. As such, the invention is of importance to the field of oncology as a whole. Furthermore, it will be readily appreciated by one familiar with the art that the diastolic decay constant for flow through a tumor can be measured from a flow waveform derived by means other than Doppler ultrasound or MRI. As such, any hemodynamic tracing which correlates with bloodflow, such as a flow tracing derived by electromagnetic flow measurement techniques, or a pressure tracing derived by intravascular catheterization, could be analyzed in a similar manner. So too, blood-flow waveforms derived by ultrasound techniques which are not based on Doppler principles (such as a technique based on evaluating the amplitude pulsation of reflected ultrasound waves), can be analyzed in a similar manner.

It will be appreciated that the above descriptions are intended only to serve as examples, and that many other embodiments are possible within the spirit and the scope of the present invention.

What is claimed is:

1. A method for diagnosing a tumor, the method comprising the steps of:
    (a) measuring a blood-flow waveform associated with the tumor, said waveform depicting pulsations of blood-flow associated with the tumor, said pulsations having systolic and diastolic components;
    (b) fitting a post-systolic portion of said blood-flow waveform to a parameterized monotonic mathematical function; and
    (c) inferring a likelihood of malignancy of said tumor from a parameter of said monotonic mathematical function.

2. The method of claim 1, further comprising the step of deriving said waveform from a measurement of a hemodynamic variable selected from the group consisting of blood velocity, blood pressure and blood flow rate.

3. The method of claim 2, wherein said hemodynamic variable is measured by a measurement technique selected from the group consisting of Doppler techniques, ultrasound techniques, Magnetic Resonance Imaging techniques, electromagnetic flow measurement techniques and intravascular catheterization techniques.

4. The method of claim 1, wherein said parameterized monotonic mathematical function is an exponential decay curve.

5. The method of claim 1, wherein said parameter of said monotonic mathematical function is a decay constant.

6. A method for diagnosing a pelvic tumor, the method comprising the steps of:
    (a) measuring a blood-flow waveform associated with the pelvic tumor, said waveform dipicting pulsations of blood-flow associated with the pelvic tumor, said pulsations having systolic and diastolic components;
    (b) fitting a post-systolic portion of said blood-flow waveform to a parameterized monotonic mathematical function; and
    (c) inferring a likelihood of malignancy of said pelvic tumor from a parameter of said monotonic mathematical function.

7. The method of claim 6, further comprising the step of deriving said waveform from a measurement of a hemodynamic variable selected from the group consisting of blood velocity, blood flow rate, and blood pressure.

8. The method of claim 7, wherein said hemodynamic variable is measured by a measurement technique selected from the group consisting of Doppler techniques, ultrasound techniques, Magnetic Resonance Imaging techniques, electromagnetic flow measurement techniques and intravascular catheterization techniques.

9. The method of claim 6, wherein said parameterized monotonic mathematical function is an exponential decay curve.

10. The method of claim 6, wherein said parameter of said monotonic mathematical function is a decay constant.

11. A system for diagnosing a tumor, the system comprising:
    (a) a mechanism for obtaining a pulsatile waveform for blood-flow associated with the tumor, said waveform having systolic and diastolic components to each pulsation,
    (b) a mechanism for fitting a post-systolic portion of said blood-flow waveform to a parameterized monotonic mathematical function; and (c) a mechanism for determining a parameter of said parameterized monotonic mathematical function, said parameter describing a likelihood of malignancy of said tumor.

12. The system of claim 11, wherein the mechanism for obtaining said blood-flow waveform includes a device selected from the group consisting of Doppler devices, ultrasound devices, Magnetic Resonance Imaging scanners, electromagnetic flow measurement devices and intravascular catheterization devices.

13. The system of claim 11, wherein the mechanism for fitting said post-systolic portion of said blood-flow waveform to said parameterized monotonic mathematical function includes a border detection algorithm.

14. A system for diagnosing a pelvic tumor, comprising:
   (a) a mechanism for obtaining a pulsatile waveform for blood-flow associated with the pelvic tumor, said waveform having systolic and diastolic components to each pulsation;
   (b) a mechanism for fitting a post-systolic portion of said blood-flow waveform to a parameterized monotonic mathematical function; and
   (c) a mechanism for determining a parameter of said parameterized monotonic mathematical function, said parameter describing a likelihood of malignancy of said pelvic tumor.

15. The system of claim 14, wherein the mechanism for generating said blood-flow waveform includes a device selected from the group consisting of Doppler devices, ultrasound devices, Magnetic Resonance Imaging scanners, electromagnetic flow measurement devices and intravascular catheterization devices.

16. The system of claim 14, wherein the mechanism for fitting the post-systolic portion of said blood-flow waveform to said parameterized monotonic mathematical function is a border detection algorithm.

* * * * *